United States Patent

Merger et al.

Patent Number: 5,304,685
Date of Patent: Apr. 19, 1994

[54] PREPARATION OF 3-(HYDROXYPHENYL)PROPIONALDE-HYDES AND THEIR HYDROGENATION TO 3-(HYDROXYPHENYL)PROPANOLS

[75] Inventors: Franz Merger, Frankenthal; Martin Schmidt-Radde, Ludwigshafen, both of Fed. Rep. of Germany

[73] Assignee: BASF Aktiengesellschaft, Ludwigshafen, Fed. Rep. of Germany

[21] Appl. No.: 37,881

[22] Filed: Mar. 26, 1993

[30] Foreign Application Priority Data

Apr. 25, 1992 [DE] Fed. Rep. of Germany ....... 4213750

[51] Int. Cl.$^5$ ...................... C07C 45/00; C07C 29/14
[52] U.S. Cl. .................................. 568/433; 568/426; 568/432; 568/852; 568/862
[58] Field of Search ............... 568/433, 426, 862, 496, 568/432

[56] References Cited

U.S. PATENT DOCUMENTS

| | | | |
|---|---|---|---|
| 4,091,225 | 5/1978 | Parker | 560/20 |
| 4,284,823 | 8/1981 | Kline | 568/433 |
| 4,317,933 | 3/1982 | Parker | 568/433 |
| 4,933,473 | 6/1990 | Ninomiya | 568/862 |
| 5,015,789 | 5/1991 | Arntz et al. | 568/862 |
| 5,093,537 | 3/1992 | Unruth et al. | 568/862 |

FOREIGN PATENT DOCUMENTS

| | | | |
|---|---|---|---|
| 0027426 | 4/1981 | European Pat. Off. | 568/433 |
| 1455766 | 11/1976 | United Kingdom | 568/433 |
| 2026479 | 2/1980 | United Kingdom | 568/433 |

Primary Examiner—Werren B. Lone
Attorney, Agent, or Firm—John H. Shurtleff

[57] ABSTRACT

A process for preparing 3-(hydroxyphenyl)propionaldehydes of the formula I

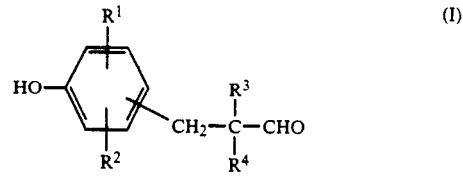

and, where appropriate, for preparing 3-(hydroxyphenyl)propanols of the formula II

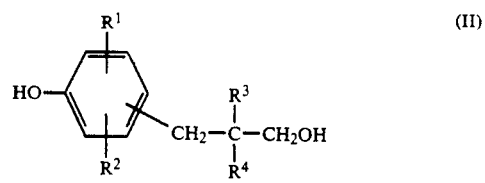

where
$R^1$, $R^2$, $R^3$ and $R^4$ are each hydrogen, $C_1$-$C_{20}$-alkyl, $C_3$-$C_{20}$-cycloalkyl, $C_4$-$C_{20}$-alkylcycloalkyl, $C_4$-$C_{20}$-cycloalkylalkyl or $C_5$-$C_{20}$-alkylcycloalkylalkyl,
$R^3$ and $R^4$ are each aryl, $C_7$-$C_{20}$-aralkyl, heterocycloalkyl or $C_3$-$C_{20}$-heterocycloalkylalkyl, entails a) reacting phenols of the formula III

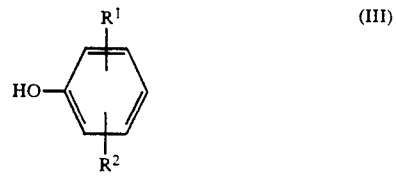

where $R^1$ and $R^2$ have the abovementioned meanings, with 3-hydroxypropionaldehydes of the formula IV (Abstract continued on next page.)

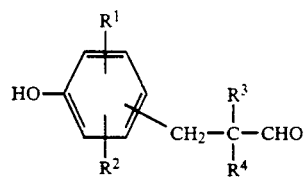

where $R^1$, $R^2$, $R^3$ and $R^4$ have the abovementioned meanings, with hydrogen in the presence of a hydrogenation catalyst at from 0° to 250° C. and under from 0.1 to 300 bar.

7 Claims, No Drawings

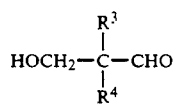

where $R^3$ and $R^4$ have the abovementioned meanings, in the presence of a basic catalyst at from 90° to 230° C. and under from 0.01 to 50 bar and, where appropriate, b) treating the resulting 3-(hydroxyphenyl)propionaldehydes of the formula I

PREPARATION OF 3-(HYDROXYPHENYL)PROPIONALDEHYDES AND THEIR HYDROGENATION TO 3-(HYDROXYPHENYL)PROPANOLS

The present invention relates to a process for preparing 3-(hydroxyphenyl)propionaldehydes by reacting phenols in the presence of a basic catalyst at elevated temperatures. The invention also relates to the preparation of the corresponding 3-hydroxyphenyl)propanols by catalytically hydrogenating the resulting 3-(hydroxphenyl)propionaldehydes in the presence of a hydrogenation catalyst.

U.S. Pat. No. 4,091,225 discloses the preparation of 3-(hydroxyphenyl)propionaldehydes I by reacting 3,5-di-t-butyl-4-hydroxybenzyl chloride with 2,2-dialkylalkanals under phase-transfer conditions.

GB-A 1 455 766 discloses the preparation of 3-(hydroxyphenyl)propionaldehydes I by the reaction, catalyzed by alkali metal hydroxide, of 3,5-dialkyl-4-hydroxybenzyl N,N-dialkyldithiocarbamates with 2,2-dialkylalkanals.

Finally, EP-A 27 426 discloses the formation of 3-(hydroxyphenyl)propionaldehydes I from 3,5-dialkyl-4-hydroxybenzyl alkyl ethers and 2,2-dialkylalkanals under the catalytic action of alkali metal hydroxides or alcoholates.

All the said processes have the disadvantage that they start from functionalized dialkylphenol derivatives which must first be prepared in elaborate syntheses from dialkylphenols.

Another disadvantage is that the catalysts must be neutralized, i.e. cannot be reused.

According to U.S. Pat. No. 4,091,225, the conversion of the 3-(hydroxyphenyl)propionaldehydes I into the 3-(hydroxyphenyl)propanols II by catalytic hydrogenation requires use of the isolated and purified 3-(hydroxyphenyl)propionaldehydes I.

It is an object of the present invention to remedy the abovementioned disadvantages.

We have found that this object is achieved by a novel and improved process for preparing 3-(hydroxyphenyl)propionaldehydes of the formula I

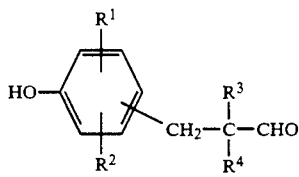

and advantageously, for preparing 3-(hydroxyphenyl)propanols of the formula II

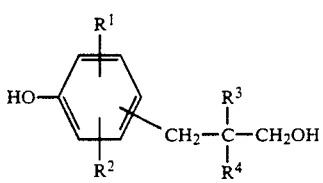

where
$R^1$, $R^2$, $R^3$ and $R^4$ are each hydrogen, $C_1$-$C_{20}$-alkyl, $C_3$-$C_{20}$-cycloalkyl, $C_4$-$C_{20}$-alkylcycloalkyl, $C_4$-$C_{20}$-cycloalkylalkyl or $C_5$-$C_{20}$-alkylcycloalkylalkyl, $R^3$ and $R^4$ are each aryl, $C_7$-$C_{20}$-aralkyl, heterocycloalkyl or $C_3$-$C_{20}$-heterocycloalkylalkyl, which comprises a) reacting phenols of the formula III

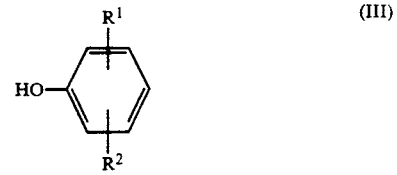

where $R^1$ and $R^2$ have the abovementioned meanings, with 3-hydroxypropionaldehydes of the formula IV

where $R^3$ and $R^4$ have the abovementioned meanings, in the presence of a basic catalyst at from 90° to 230° C. and under from 0.01 to 50 bar and, where appropriate, b) treating the resulting 3-(hydroxyphenyl)propionaldehydes of the formula I

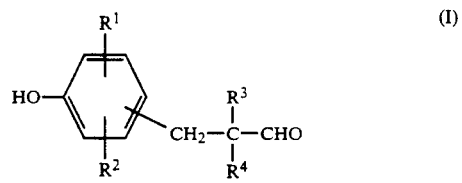

where $R^1$, $R^2$, $R^3$ and $R^4$ have the abovementioned meanings, with hydrogen in the presence of a hydrogenation catalyst at from 0° to 250° C. and under from 0.1 to 300 bar.

The process according to the invention can be carried out in the following way:

a) The phenols III can be reacted with 3-hydroxypropionaldehydes IV in the presence of a basic catalyst and, preferably, with the addition of an inert solvent at from 90° to 230° C., preferably 110° to 210° C., particularly preferably 140° to 190° C., and under from 0.01 to 50 bar, preferably 0.1 to 5 bar, particularly preferably under the autogenous pressure of the system.

The reaction time depends on the substitution pattern of the dialkylphenol and is usually from 0.2 to 200 h.

The reaction can be carried out batchwise or continuously, preferably batchwise, and it is possible to use all conventional reactors.

The molar ratio of phenol III to 3-hydroxypropionaldehyde IV is usually in the range from 0.5:1 to 1.5:1, preferably 0.8:1 to 1.2:1.

Examples of suitable basic catalysts are amines, preferably secondary amities. Suitable secondary amines are heterocyclic, aliphatic and cycloaliphatic amines with 2-20 carbons, preferably 4-15 carbons, and aliphatic secondary amines are preferably employed. Examples which may be mentioned are the following: dimethylamine, diethylamine, di-n-propylamine, diisopropylamine, di-n-butylamine, diisobutylamine, methyethylamine, methyl-n-propylamine, methylisopropylamine, methyl-n-butylamine, methylisobutylamine, ethyl-n-propylamine, ethylisopropylamine, ethyl-n-butylamine, methylcyclohexylamine, pyrrolidine, piperidine, piperazine, morpholine, N-methylethanolamine and diethanolamine.

The molar ratio of basic catalyst to the 3-hydroxypropionaldehyde IV is usually in the range from 0.01:1 to 0.5:1, preferably 0.05:1 to 0.25:1. Larger amounts of catalyst are possible but usually provide no advantages.

The 3-hydroxypropionaldehydes IV can be prepared as described, for example, in DE-A 1 793 512 and DE-A 1 957 301 from aldehydes with a beta hydrogen atom and aqueous formaldehyde with catalysis by trialkylamine. Both the crude product and the purified product of the reaction of the particular aldehyde with formaldehyde are suitable in this case. 3-Hydroxypropionaldehydes IV with a water content of from 0 to 50% by weight, preferably 4 to 20% by weight, are normally used.

Suitable inert solvents are inert organic solvents, which are preferably readily miscible with water. Examples which may be mentioned are: (cyclic) ethers such as tetrahydrofuran and dioxane, as well as $C_1$–$C_{30}$-alkanols such as methanol, ethanol, propanol, isopropanol, ethylene glycol, propylene glycol, ethylene glycol monoethyl ether, methyl glycol. $C_1$–$C_3$-Alkanols are particularly preferred.

The amount of solvent should be such that the content of solvent in the reaction mixture is from 5 to 95% by weight, preferably 40 to 90% by weight.

The 3-(hydroxyphenyl)propionaldehydes I can be isolated from the reaction mixture in a simple way by conventional methods, for example distillation and/or crystallization.

b) It is especially advantageous for the resulting 3-(hydroxphenyl)propionaldehydes I to be treated in the presence of a hydxogenation catalyst, preferably a heterogeneous catalyst, with hydrogen at from 0° to 250° C., preferably 20° to 200° C., and under from 0.1 to 300 bar, preferably 1 to 200 bar. It is possible for the hydrogenation catalyst to be suspended in the reaction mixture or arranged in a fixed bed.

It is possible in principle to use all conventional hydrogenation catalysts for hydrogenating the 3-(hydroxphenyl)propionaldehydes I to the 3-(hydroxyphenyl)-propanols II, for example catalysts containing nickel, cobalt, copper, manganese, molybdenum, rhenium and/or the platinum metals palladium, platinum and ruthenium. It is possible in this connection to employ both the pure metals, finely divided or in the form of networks or other structures of high surface area, and catalysts which contain a plurality of these metals. The hydrogenation catalysts can be employed in unsupported or in supported form. Conventional support materials can be used for supported catalysts, such as silica, aluminas, zirconium dioxide, titanium dioxides, active carbon, barium sulfate, barium carbonate, calcium carbonate and the like. Preferably employed in the process according to the invention are nickel- and/or copper- and/or cobalt-containing and/or ruthenium catalysts. Nickel and ruthenium catalysts are particularly preferred, for example Raney nickel and ruthenium/active carbon.

The 3-(hydroxyphenyl)propanol II can be isolated from the hydrogenation mixture by conventional methods, for example distillation and/or crystallization.

The substituents $R^1$, $R^2$, $R^3$ and $R^4$ in the compounds of the formulae I and II have the following meanings:

$R^1$, $R^2$, $R^3$, $R^4$ independently of one another hydrogen, $C_1$–$C_{20}$-alkyl, preferably $C_1$–$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, particularly preferably $C_1$–$C_4$-alkyl such as methyl, ethyl, n-propyl, isopropyl, n-butyl, isobutyl, sec-butyl and tert-butyl, $C_3$–$C_{20}$-cycloalkyl, preferably $C_3$–$C_8$-cycloalkyl such as cyclopropyl, cyclobutyl, cyclopentyl, cyclohexyl, cycloheptyl and cyclooctyl, particularly preferably cyclopentyl, cyclohexyl and cyclooctyl, $C_4$–$C_{20}$-alkylcycloalkyl, preferably 2, 6-dimethylcyclohexyl, $C_4$–$C_{20}$-cycloalkyalkyl, preferably cyclopropylmethyl, cyclobutylmethyl, cyclopentylmethyl and cyclohexylmethyl, $C_5$–$C_{20}$-alkylcycloalkylalkyl, $R^3$, $R^4$ aryl such as phenyl, 1-naphthyl, 2-naphthyl, 9-naphthyl and biphenylyl, preferably phenyl, $C_7$–$C_{20}$-aralkyl, preferably $C_7$–$C_{12}$-aralkyl such as benzyl, phenylethyl, 1-naphthylmethyl and biphenylylmethyl; heterocycloalkyl such as a 5- or 6-membered ring with one or two O, N and/or S atoms in the ring, which can be aromatic or non-aromatic, such as 2- or 3-furyl, 2- or 3-thienyl, 2- or 3-pyrrolyl, 2- or 4-imidazolyl, 2- or 3-oxazolyl, 2- or 3-thiazolyl, pyridinyl, morpholyl, thiomorpholyl or pyrazolyl, $C_3$–$C_{20}$-heterocycloalkylalkyl.

Suitable and preferred phenols III are those which are 2,6- or 2,4-dialkyl-substituted, where $R^1$ and $R^2$ are each, independently of one another, alkyl with 1 to 6 carbons or a cycloaliphatic radical with 4 to 12 carbons.

Examples of suitable dialkylphenols III are 2,6-dimethyl-, 2,6-diethyl-, 2,6-di-n-propyl-, 2,6-diisopropyl-, 2,6-di-n-butyl-, 2,6-diisobutyl-, 2,6-di-t-butyl-, 2,4-dimethyl-, 2,4-diethyl-, 2,4-di-n-propyl-, 2,4-diisopropyl-, 2,4-di-n-butyl-, 2,4-diisobutyl-, 2,4-di-t-butyl-, 2-methyl-6-ethyl-, 2-methyl-6-isopropyl-, 2-methyl-6-t-butyl-, 2-methyl-4-ethyl-, 2-methyl-4-isopropyl-, 2-methyl-4-t-butyl-phenol.

Preferred 3-hydroxypropionaldehydes IV are betahydroxy aldehydes, for example 2,2-dimethyl-3-hydroxypropanal, 2-ethyl-2-methyl-3-hydroxypropanal, 2-methyl-2-propyl-3-hydroxypropanal, 2-butyl-2-methyl-3-hydroxypropanal, 2-butyl-2-ethyl-3-hydroxypropanal, 2-ethyl-2-propyl-3-hydroxypropanal, 2-ethyl-2-hexyl-3-hydroxypropanal, 2-ethyl-2-isopropyl-3-hydroxypropanal, 2-methyl-2-phenyl-3-hydroxypropanal, 2-methyl-2-(alphanaphthyl)-3-hydroxypropanal, 2-cyclohexyl-2-methyl-3-hydroxypropanal, 2-ethyl-2-cyclohexyl-3-hydroxypropanal, 2-hydroxymethylcyclopentane-, 2-hydroxymethylcyclohexane-, 2-hydroxymethylcyclooctane-, 2-hydroxymethylcyclodecane-carboxaldehyde, 2-methyl-2-pyridyl-3-hydroxypropanal, 2-furyl-2-methyl-3-hydroxypropanal.

The 3-(hydroxyphenyl)propionaldehydes I are intermediates with a wide variety of uses (aminophenols, carbonates, polymer components).

The 3-(hydroxyphenyl)propanols II can be used as antioxidants which can be incorporated in polymers.

EXAMPLES

Example 1

125 g (1 mol) of 80% strength aqueous 2,2-dimethyl-3-hydroxypropanal (crude mixture from the synthesis, reduced to a water content of 20% by distillation), 109 g (0.9 mol) of 2,6-dimethylphenol, 12 g (0.11 mol) of 40% strength aqueous dimethylamine and 700 g of methanol are reacted in a stirred autoclave at 180° C. and under the autogenous pressure of 20-30 bar for 10 h. Workup of the reaction mixture by distillation yields 168 g (91%) of 3-(3,5-dimethyl-4-hydroxyphenyl)-2,2-dimethylpropanal (boiling point 140°-142° C.; melting point 72°-73° C.).

Example 2

125 g (1 mol) of 80% strength aqueous 2,2-dimethyl-3-hydroxypropanal (crude mixture from the synthesis, reduced to a water content of 20% by distillation), 185 g (0.9 mol) of 2,6-di-t-butylphenol, 12 g (0.11 mol) of 40% strength aqueous dimethylamine and 700 g of methanol are reacted in a stirred autoclave at 180° C. and under the autogenous pressure of 20-30 bar for 10 h. Workup of the reaction mixture by distillation yields 238 g (92%) of 3-(3,5-di-t-butyl-4-hydroxyphenyl)-2,2-dimethylpropanal (boiling point 126°-127° C.; melting point 75°-77° C.).

Example 3

125 g (1 mol) of 80% strength aqueous 2,2-dimethyl-3-hydroxypropanal (crude mixture from the synthesis, reduced to a water content of 20% by distillation), 185 g (0.9 mol) of 2,4-di-t-butylphenol, 24 g (0.22 mol) of 40% strength aqueous dimethylamine and 700 g of methanol are reacted in a stirred autoclave under autogenous pressure of 20-30 bar at 160° C. for 20 h and then at 180° C. for 20 h. Workup of the reaction mixture by distillation yields 159 g (61%) of 3-(3,5-di-t-butyl-2-hydroxyphenyl)-2,2-dimethylpropanal (boiling point 115°-116° C.).

Example 4

125 g (1 mol) of 80% strength aqueous 2,2-dimethyl-3-hydroxypropanal (crude mixture from the synthesis, reduced to a water content of 20%. by distillation), 109 g (0.9 mol) of 2,6-dimethylphenol, 12 g (0.11 mol) of 40% strength aqueous dimethylamine and 700 g of methanol are reacted in a stirred autoclave at 180° C. under autogenous pressure of 20-30 bar for 10 h. After the autoclave has cooled and the pressure has been released, 19 g of Raney Ni (0.02 parts based on complete mixture) are added to the reaction mixture and hydrogenation is carried out at 80° C. under 80 bar of hydrogen for 5 h. Workup of the mixture by distillation yields 174 g (92%) of 3-(3,5-dimethyl-4-hydroxyphenyl)-2,2-dimethylpropanol (boiling point 172°-174° C.; melting point 133°-134° C.).

Example 5

125 g (1 mol) of 80% strength aqueous 2,2-dimethyl-3-hydroxypropanal (crude mixture from the synthesis, reduced to a water content of 20% by distillation), 185 g (0.9 mol) of 2,6-di-t-butylphenol, 12 g (0.11 mol) of 40% strength aqueous dimethylamine and 700 g of methanol are reacted in a stirred autoclave at 180° C. under autogenous pressure of 20-30 bar for 10 h. After the autoclave has cooled and the pressure has been released, 28 g of Raney Ni (0.03 parts based on complete mixture) are added to the reaction mixture and hydrogenation is carried out at 80° C. under 80 bar of hydrogen for 5 h. Workup of the mixture by distillation yields 239 g (91%) of 3-(3,5-di-t-butyl-4-hydroxyphenyl)-2,2-dimethylpropanol (boiling point 142°-145° C.; melting point 84°-86° C.).

Example 6

125 g (1 mol) of 80% strength aqueous 2,2-dimethyl-3-hydroxypropanal (crude mixture from the synthesis, reduced to a water content of 20% by distillation), 109 g (0.9 mol) of 2,4-dimethylphenol, 24 g (0.22 mol) of 40% strength aqueous dimethylamine and 700 g of methanol are reacted in a stirred autoclave under autogenous pressure of 20-30 bar at 160° C. for 20 h and then at 180° C. for 20 h. After the autoclave has cooled and the pressure has been released, 95 g of Raney Ni (0.1 parts based on complete mixture) are added to the reaction mixture and hydrogenation is carried out at 140° C. under 80 bar of hydrogen for 20 h. After filtration and removal of volatiles by distillation, the residue is recrystallized from methanol/water 10:3. 112 g (60%) of 3-(3,5-dimethyl-2-hydroxyphenyl)-2,2-dimethylpropanol are obtained (melting point 117° C.).

We claim:

1. A process for preparing 3-(hydroxyphenyl)propionaldehydes of the formula I

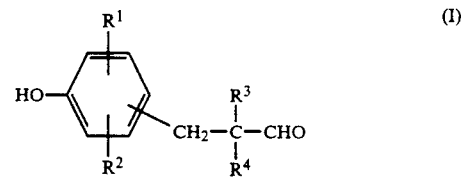

where
$R^1$, $R^2$, $R^3$ and $R^4$ are each hydrogen, $C_1$–$C_{20}$-alkyl, $C_3$–$C_{20}$-cycloalkyl, $C_4$–$C_{20}$-alkylcycloalkyl, $C_4$–$C_{20}$-cycloalkylalkyl or $C_5$–$C_{20}$-alkylcycloalkylalkyl, $R^3$ and $R^4$ are each aryl, $C_7$–$C_{20}$-aralkyl, heterocycloalkyl or $C_3$–$C_{20}$-heterocycloalkylalkyl, which comprises a) reacting phenols of the formula III

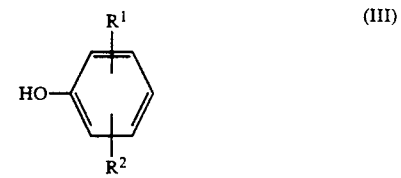

where $R^1$ and $R^2$ have the abovementioned meanings, with 3-hydroxypropionaldehydes of the formula IV

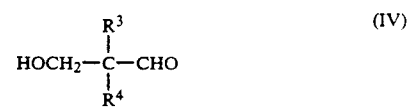

where $R^3$ and $R^4$ have the abovementioned meanings, in the presence of a basic catalyst at from 90° to 230° C. and under from 0.01 to 50 bar.

2. A process for preparing 3-(hydroxyphenyl)propionaldehydes I as claimed in claim 1, wherein the reaction is carried out at from 110° to 210° C.

3. A process for preparing 3-(hydroxyphenyl)propionaldehydes I as claimed in claim 1, wherein the reaction is carried out under from 0.1 to 5 bar.

4. A process for preparing 3-(hydroxyphenyl)propionaldehydes I as claimed in claim 1, wherein amines are used as basic catalysts.

5. A process for preparing 3-(hydroxyphenyl)propionaldehydes I as claimed in claim 1, wherein secondary amines are used as basic catalysts.

6. A process as claimed in claim 1, wherein the 3-(hydroxyphenyl)propionaldehyde I obtained as the product in a first step is hydrogenated in a second step by reaction with hydrogen in the presence of a hydrogenation catalyst at from 0° to 250° C. and under from 0.1 to 300 bar to obtain the corresponding 3-(hydroxyphenyl)propanol of the formula II

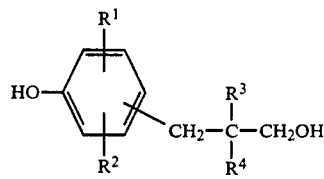

(II)

where $R^1$, $R^2$, $R^3$ and $R^4$ have the same meanings as in claim 1.

7. A process as claimed in claim 6, wherein the reaction mixture containing the 3-(hydroxyphenyl)propionaldehyde product in the first step is directly hydrogenated in the second step without distillation or other purification steps.

* * * * *

UNITED STATES PATENT AND TRADEMARK OFFICE
CERTIFICATE OF CORRECTION

PATENT NO. : 5,304,685
DATED : April 19, 1994
INVENTOR(S) : Merger et al.

It is certified that error appears in the above-identified patent and that said Letters Patent is hereby corrected as shown below:

IN THE ABSTRACT (Title page, item [57])

Please amend the Abstract as shown by the Amendment dated October 11, 1993 to read as follows:

-- A process for the preparation of 3-(hydroxyphenyl)propionaldehyde by reacting a phenol with a 3-hydroxypropionaldehyde in the presence of a basic catalyst at a temperature of from 90 to 230°C and under a pressure of from 0.01 to 50 bar, and advantageously hydrogenating the resulting 3-(hydroxyphenyl)-propionaldehyde product with hydrogen in the presence of a hydrogenation catalyst at a temperature of from 0 to 250°C and under a pressure of from 0.1 to 300 bar.--

Signed and Sealed this

Eleventh Day of October, 1994

Attest:

BRUCE LEHMAN

*Attesting Officer*     *Commissioner of Patents and Trademarks*